US011484412B2

(12) United States Patent
Link

(10) Patent No.: US 11,484,412 B2
(45) Date of Patent: Nov. 1, 2022

(54) COATING FOR AN IMPLANT

(71) Applicant: Waldemar Link GmbH & Co. KG, Hamburg (DE)

(72) Inventor: Helmut D. Link, Hamburg (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 320 days.

(21) Appl. No.: 16/327,224

(22) PCT Filed: Aug. 11, 2017

(86) PCT No.: PCT/EP2017/070439
§ 371 (c)(1),
(2) Date: Feb. 21, 2019

(87) PCT Pub. No.: WO2018/036843
PCT Pub. Date: Mar. 1, 2018

(65) Prior Publication Data
US 2019/0209330 A1     Jul. 11, 2019

(30) Foreign Application Priority Data
Aug. 22, 2016 (EP) .................................... 16185135

(51) Int. Cl.
*A61F 2/32* (2006.01)
*A61F 2/30* (2006.01)
(Continued)

(52) U.S. Cl.
CPC ........ *A61F 2/30771* (2013.01); *A61L 27/042* (2013.01); *A61L 27/045* (2013.01);
(Continued)

(58) Field of Classification Search
CPC ........ A61L 27/06; A61L 27/045; A61F 2/605; A61F 2007/004; A61F 2/32;
(Continued)

(56) References Cited

U.S. PATENT DOCUMENTS 5,282,861 A * 2/1994 Kaplan ................. A61L 27/306
                                                       623/23.51
6,371,985 B1 * 4/2002 Goldberg ............. A61F 2/4241
                                                       623/23.57
(Continued)

FOREIGN PATENT DOCUMENTS

CN      101862231 A     10/2010
CN      201668538 U     12/2010
(Continued)

OTHER PUBLICATIONS

International Search Report and Written Opinion dated Oct. 10, 2017 in corresponding International Application No. PCT/EP2017/070439.
(Continued)

*Primary Examiner* — Seema Mathew
(74) *Attorney, Agent, or Firm* — Chiesa Shahinian & Giantomasi

(57) ABSTRACT

The present invention relates to an implant (10) comprising an implant body having a first surface area (A1, A2, A3, A4) configured for contact with soft connective tissue and a second surface area configured for contact with bone tissue, wherein the first surface area is covered with a coating comprising tantalum and the second surface area is formed by a material, which is different than the one forming the coating.

10 Claims, 2 Drawing Sheets

(51) Int. Cl.
*A61L 27/04* (2006.01)
*A61L 27/06* (2006.01)
*A61L 27/30* (2006.01)
*C23C 4/134* (2016.01)
*C23C 4/08* (2016.01)

(52) U.S. Cl.
CPC ............. *A61L 27/047* (2013.01); *A61L 27/06* (2013.01); *A61L 27/306* (2013.01); *A61F 2/32* (2013.01); *A61F 2002/3092* (2013.01); *A61F 2310/00017* (2013.01); *A61F 2310/00023* (2013.01); *A61F 2310/00029* (2013.01); *A61F 2310/00101* (2013.01); *A61F 2310/00544* (2013.01); *A61L 2420/02* (2013.01); *A61L 2430/02* (2013.01); *C23C 4/08* (2013.01); *C23C 4/134* (2016.01)

(58) Field of Classification Search
CPC .. A61F 2002/30998; A61F 2002/30995; A61F 2310/00101; A61F 2310/00544; A61F 2310/00023
See application file for complete search history.

(56) References Cited

U.S. PATENT DOCUMENTS

| | | | | |
|---|---|---|---|---|
| 7,077,867 | B1* | 7/2006 | Pope | B22F 7/06 623/20.14 |
| 2006/0287733 | A1* | 12/2006 | Bonutti | A61B 90/94 623/908 |
| 2009/0061388 | A1* | 3/2009 | Collins | A61C 8/005 433/174 |
| 2010/0094430 | A1* | 4/2010 | Krumdieck | A61F 2/30767 427/2.27 |
| 2012/0101592 | A1* | 4/2012 | Thomas | A61F 2/28 156/308.2 |
| 2013/0197649 | A1* | 8/2013 | Lambert | A61L 27/306 623/18.11 |
| 2014/0004356 | A1 | 1/2014 | Vargas et al. | |
| 2017/0156869 | A1* | 6/2017 | Uzuyem | A61F 2/32 |
| 2018/0028321 | A1* | 2/2018 | Zhu | A61L 27/28 |

FOREIGN PATENT DOCUMENTS

| | | | |
|---|---|---|---|
| CN | 203 280 542 U | 11/2013 | |
| CN | 103 451 602 A | 12/2013 | |
| RU | 2040277 C1 | 7/1995 | |
| RU | 2142819 C1 | 12/1999 | |
| RU | 2313370 C2 | 12/2007 | |
| RU | 2549984 C1 | 5/2015 | |
| RU | 2554819 C1 | 6/2015 | |
| WO | WO-2012050837 A1 * | 4/2012 | ............... A61F 2/28 |
| WO | WO 2016/126789 A1 | 8/2016 | |

OTHER PUBLICATIONS

Gee et al., "Current Evidence and Future Directions for Research into the Use of Tantalum in Soft Tissue Re-Attachment Surgery," Journal of Materials Chemistry B, v.4(6), Jan. 1, 2016, p. 1020-1034.

Examination Report dated Sep. 7, 2020 in corresponding European Application No. 16 185 135.7.

Chinese Journal of Clinical Anatomy, vol. 30, No. 1, pp. 114-116, "Progress in Research of Biomaterial Properties of Porous Tantalum Applied in Orthopedic Department".

Office Action issued in the corresponding Chinese Patent Application No. 201780058239.6 dated Dec. 31, 2020 and its English Translation.

Search Report issued in the corresponding Russian Application No. 2019108058 dated Nov. 10, 2020 and its English Translation.

* cited by examiner

COATING FOR AN IMPLANT

CROSS-REFERENCE TO RELATED APPLICATIONS

This application is the National Stage entry under 35 U.S.C. § 371 of International Application No. PCT/EP2017/070439 filed on Aug. 11, 2017, published on Mar. 1, 2018 under Publication Number WO 2018/036843, which claims the benefit of priority under 35 U.S.C. § 119 of European Patent Application Number 16185135.7 filed Aug. 22, 2016, the entireties of which are herein incorporated by reference.

TECHNICAL FIELD

The present invention relates to a coating for an implant with an implant body that is configured for contact with soft connective tissue and bone tissue as well as to a method for producing such an implant.

BACKGROUND OF THE INVENTION

One of the big advances in orthopedic surgery is the apposition of bone tissue on implants that provides a strong and durable integration of these implants within a skeletal structure. Typical materials used for such implants are titanium alloys, CoCr alloys and stainless steel. In this respect, titanium plays a vital role due to its biocompatibility and positive effect on osteoblasts in terms of creation of bone tissue on an implant's surface. As a result, titanium and in particular titanium alloys are frequently used as structural material for implants that substitute or are anchored in bone such as endoprosthetic implants.

Besides choosing the right material for these implants which has the required mechanical characteristics as well as biocompatibility, the implant's surface topography, i.e. the surface of the structural material of the implant body or any coating on its surface, also significantly influences the integration with bone tissue.

Before implantation, the implantation site commonly requires the detachment of soft connective tissue, in particular ligaments and tendons. It is sometimes desirable to attach at least parts of this soft connective tissue in order to keep or restore the mobility and functionality of the skeletal structure and the position of the implant as much as possible. The removal of soft connective tissue structures particularly occurs if bone tissue is to be replaced by an implant, for example due to implantation of a bone or joint prosthesis or bone tissue that has been affected by a tumor.

One technique to maintain soft connective tissue structures, is to separate these structures along with the periosteum including any vessels from the bone tissue and to use the periosteum including these structures after implantation in order to cover the exposed parts of the implant. With this technique, soft connective tissue structures attached to the periosteum can be maintained. However, once covering the implant, tensile forces through these soft connective tissue structures, such as muscle forces, cannot be properly transmitted to the implant since the periosteum is normally attached using surgical methods, for example sutures or glue. In other words, although this technique has the potential to reattach at least parts of the soft connective tissue to an implant, the periosteum merely covers the implant so that there is insufficient anchorage or attachment of the soft connective tissue to the latter. Further, maintaining soft connective tissue helps to keep the implant in place. This is particularly of interest if the bone anchorage of the implant is insufficient.

SUMMARY OF THE INVENTION

Thus, an objective of the invention was to provide an implant having a surface that provides an improved environment for soft connective tissue and facilitates an attachment of these structures to the implant In relation to this invention, soft connective tissue refers particularly to connective tissue that normally attaches muscles or other tissues to bone tissue.

Consequently, bone tissue is not considered as being soft connective tissue in relation to the present invention. In particular, the term soft connective tissue refers to dense regular connective tissue, which forms organized structures and is a major functional component of tendons, ligaments and aponeuroses. Dense connective tissue is a type of connective tissue with collagen I fibers as its main matrix element. Crowded between the collagen fibers are rows of fibroblasts which are fiber-forming cells that generate the fibers.

In order to fulfill the above-noted objective, the invention provides an implant comprising an implant body with a first surface area configured for contact with soft connective tissue and a second surface area configured for contact with bone tissue, wherein the first surface area is covered by a coating comprising tantalum and the second surface area is formed by a material, which is different than the one of the coating covering the first surface area.

The inventors realized that a coating comprising tantalum has a positive effect on the behavior and survival of fibroblasts and that a coating as described herein is particularly valuable when being applied to an implant replacing at least a part of the pelvis. The coating may be formed by pure tantalum or a tantalum alloy.

Without wishing to be bound by any particular theory, it is believed that the observed effect of an improved environment for soft connective tissue attachment in the area of the pelvis is augmented because of a particularly advantageous ratio of fibroblast forming soft connective tissue material in that area of the body on the one hand and a relatively large surface area of the implant that is available for the attachment of soft connective tissue on the other hand. This effect may also result in improved support of the implant, which is particularly advantageous in case of insufficient bone anchorage.

Further, configuring the first surface area using a coating comprising tantalum provides the advantage of a great adaptability of the first surface area, i. e. the outer surface of the first surface area, in order to achieve the surface characteristics that support the attachment of the soft connective tissue structures. This may be supplemented by controlling the application of the coating to adapt the surface parameters such as porosity, surface structure, and surface roughness for providing an environment on the surface of an implant allowing the soft connective tissue to connect. Alternatively or additionally, the first surface area, on which the coating is to be applied, can be processed beforehand to obtain the desired surface parameters. In other words, the surface topography is created on the implant body in the first surface area before the coating is applied. This may be done using another coating, directly modifying the outer surface of the implant body and/or directly creating the implant body with the desired surface topography, e. g. by using additive manufacturing. Creating the surface topography on the implant body before applying the coating comprising tantalum has cost advantages since the tantalum coating only has to be applied as a thin layer It is particularly preferred that the first surface area is adapted so that it has a topography that allows for the attachment of soft connective tissue to the implant. Also, when providing the first surface area with a surface topography that configures this area for an attachment of soft connective tissue, the mechanical properties of the first surface area can be adapted to be closer to the mechanical properties of the soft connective tissue structures.

Combined with a second surface area that is configured for contact with bone, an implant according to the invention provides the boundary conditions for an integration of both bone tissue and soft connective tissue over time, preferably dependent on the location of the implant. This enhances the overall functionality the implant can provide to the implantation site. In the long term, the implant can be securely anchored to adjacent bone tissue, and the connection to soft connective tissue structures, in particular dense regular connective tissue, can be achieved. Consequently, the present invention is particularly applicable for joint implants or endoprostheses. The present invention is also advantageous if the anchorage to remaining bone is insufficient for the transfer of functional loads since anchorage is assisted by the attachment of soft connective tissue.

In relation to this invention, an implant comprises an implant body with at least a first and a second surface area. Consequently, there may well be another surface area if the first surface area and the second surface area do not cover the entire surface of the implant or implant body. For example, a third surface area may be provided with a smooth or polished surface in order to support internal organs without triggering any attachment or injury of such tissue.

In a preferred embodiment of the implant, the coating covering the first surface area consists of pure tantalum.

The application of pure tantalum as coating turned out to have an outstanding biocompatibility for fibroblasts and, as a result, can establish an improved attachment to above-mentioned soft connective tissue structures.

In a particularly preferred embodiment of the present invention, the implant is a replacement for at least a part of the pelvis.

The pelvis comprises the acetabulum of the hip joint, which is formed by parts of the ilium, the ischium and the pubis, and is a frequently replaced joint. When replacing a native hip joint for the first time, generally only a minor intervention is required in order to attach the cup of a hip implant to the pelvis or acetabulum. However, this may change in case of a revision, i.e. an existing hip implant has to be replaced with a new one. Since a revision requires the removal of the old hip component, a larger portion or all of the acetabulum and probably neighboring structures have to be removed.

The removal of this bone tissue from the pelvis may increase due to an infection or tumorous tissue. In particular in the latter situation, the detachment of soft connective tissue structures may significantly affect the support function, stability and movability of the skeletal structure. As a result, applying the present invention to a pelvis is particularly advantageous since it helps restoring the stability and functionality of the implantation site after surgery. However, the invention is generally applicable to any implant that profits from soft connective tissue attachment.

In yet another preferred embodiment, the first surface area covers at least 30%, preferably at least 50%, more preferably at least 70%, and most preferably the entire surface of the implant except for the second surface area.

As a result, it is particularly preferred to apply the coating forming the first surface substantially on the entire surface of the implant except for the part, where the second surface area is located. It is advantageous to maximize the part of the implant's surface covered with the first surface area since this generally results in an increased strength of the connection to the implant and an improved anchoring.

In another preferred embodiment, the second surface area is formed by the material forming the implant body.

This embodiment builds on the experience with materials that have been used so far in order to replace a part of a skeletal structure with an implant, such as a joint and/or bone tissue. Primarily, these materials are optimized for providing the structural stability and functionality to serve as a replacement of native tissue. They may enhance integration between bone tissue and the implant, i.e. apposition of bone tissue to the implant's surface. In other words, the outer surface of the second surface area in this embodiment is not formed as a coating but is established by the basic material or metal alloy forming the prosthesis or general shape of the prosthesis.

In a preferred embodiment of the implant, the first surface area comprises a surface topography that is generally formed or provided by the surface of the implant lying underneath the coating.

This has the advantage that the topography of the first surface area, such as a surface roughness or porosity, can already be formed on the surface of the basic material forming the implant body before applying the coating. This basically eliminates the risk that the coating is damaged when creating the desired surface topography on the basis of the coating. In other words, the coating covers the surface topography of the implant body but has a thickness that leaves the surface topography of the implant body intact. Also, By adding a coating to the first surface area of the implant, the implant can be configured for an enhanced apposition of soft connective tissue but may keep a surface topography providing the ability for bone ingrowth.

In a particularly preferred embodiment, the coating of the first surface area has a thickness of 2 to 10 μm, preferably 2 to 5 μm.

This range for the thickness of the coating is sufficient to reliably cover an outer surface portion of the implant. It is also possible to apply the coating to an existing surface topography without causing a substantial change in its characteristics.

In another preferred embodiment, the structural material forming the second surface area comprises titanium, CoCr, Mo, alloys thereof, and stainless steel.

These materials are well-established and highly biocompatible materials in the arts. In particular titanium has shown to be suitable for achieving apposition of bone tissue. In addition, the inventors determined that any of those materials can serve as a base material for the coating applied to the first surface area. The connection between coating and base material provides sufficient strength to transfer any forces that, once implanted, are applied from the soft connective tissue to the implant.

In a particularly preferred embodiment, the second surface area has the same surface topography as the first surface area.

Basically, the surface topography of the first surface area allows for a good integration between the soft connective tissue and the implant's outer surface. On the other hand, the same surface topography is applied to the second surface area, where it enhances ingrowth of bone tissue and, thus, forms a strong bone-implant-interface.

In another preferred embodiment, the first and/or second surface area is porous, preferably with a pore size of 40 to 800 μm.

A porous surface has advantageous characteristics for bone apposition, in particular with pores generally having a size in the above noted range. Nonetheless, these pores may also serve to establish a mechanical connection with soft connective tissue when being situated in the first surface area, i. e. when being coated with above mentioned coating.

According to another preferred embodiment, the first surface area has an average surface roughness $R_a$ in the range of 2 to 3 μm and at maximum 7 μm, preferably 5 μm.

These values have been found to provide an environment that allows contact between the first surface area and soft connective tissue structures without affecting the fibroblasts that produce the extracellular matrix of these structures. The roughness of the surface topography provides sufficient support for these structures to be anchored and enough surface structure for a mechanical connection.

The present invention also provides a method for producing an implant, the method comprising the steps of providing an implant body that establishes the general shape of the implant, wherein the implant body has a first and a second surface area, the second surface area being configured for contact with bone tissue, applying a coating comprising tantalum the implant body's first surface area, wherein the first surface area is configured for contact with soft connective tissue and the second surface area comprises a material that differs from the one of the first surface area.

The implant body is made of a biocompatible material, preferably a metal alloy comprising at least one of the above listed components and more preferably a titanium alloy, wherein the material preferably forms the outer surface of the second surface area. As detailed above, this has the advantage that for fulfilling the primary function of an implant, i.e. the replacement of bone tissue and/or a joint, the implant according to the present invention can make use of a structural design that has proven to be effective in this respect.

By the application of a coating comprising tantalum to the first surface area and, thus, forming the outer surface of the first surface area, complements the implant in that this part of the implant is configured for the attachment of soft connective tissue structures. This attachment comprises at least an ECM attachment (extracellular matrix) that provides the mechanical strength for the connection between the soft connective tissue and the implant. The mechanical connection can be enhanced by a structural modification of the surface such as Trabeculink® or a metal cellular structure. As noted above, the structural modification can either be achieved by the coating itself or is established by the surface of the implant body or another coating underneath the coating that comprises tantalum. In both cases the coating provides a biocompatible surface for attachment of the soft tissue structures.

According to another preferred embodiment, the method further comprises the step of abrasive blasting, in particular grit blasting, the first surface area for creating an average surface roughness $R_a$ in the range of 2 to 3 μm and at maximum 7 μm, preferably 5 μm.

Using abrasive blasting, in particular grit blasting, creates a surface environment for fibroblasts that fosters the attachment of soft connective tissue to the implant by forming the surface characteristics as described above. Preferably, this step is applied to the material of the implant body to provide the surface topography for enhancing the attachment of soft connective tissue to the coated first surface area of the implant.

According to another embodiment, the coating is applied using vacuum deposition, such as chemical vapor deposition and/or physical vapor deposition, in particular with the use of plasma, and/or thermal spraying, in particular plasma spraying.

These techniques have been found to attach the coating forming the first surface area with sufficient strength and thickness. Further, both techniques provide a uniform coating despite the preferably rather complex rough surface geometry of the implant's surface, in particular if this surface is porous. The application of plasma spraying and/or additive manufacturing, such as for forming a Trabeculink® structure, allows for the creation of a porous surface structure that has an advantageous effect on the mechanical anchoring of the soft connective tissue.

SHORT DESCRIPTION OF THE FIGURES

The following figures illustrate preferred embodiments of the present invention. These embodiments are not to be construed as limiting but merely to enhance the understanding of the invention together with the following description. In these figures, same reference signs refer to features throughout the drawings that have the same or an equivalent function and/or structure. In summary, the figures illustrate the following:

FIG. 3a shows a schematic view of the muscles attached to the anterior side of the pelvis, whereas FIGS. 3b and 3c illustrate the muscle layers attached to the posterior side of the pelvis.

DETAILED DESCRIPTION OF PREFERRED EMBODIMENTS

Figure 1:
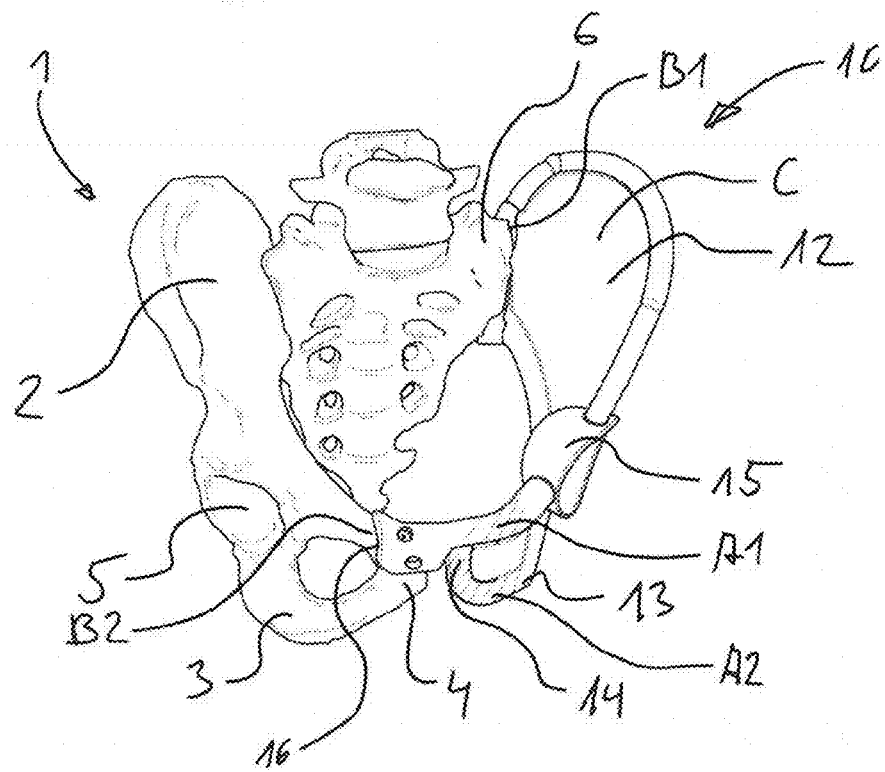
FIG. 1 shows an exemplary embodiment of an implant replacing at least parts of a pelvis viewed from anterior.

FIG. 1 is an illustration of the skeletal structure of the pelvis, wherein the left side of the pelvis has been replaced by an implant comprising a coating according to the present invention. The right side of the pelvis is still formed by native bone tissue. It comprises the ilium 2, the ischium 3, the pubic bone 4, and the acetabulum 5 of the pelvis 1. The ilium is connected via the sacroiliac joint to the sacrum 6, which in turn is adjacent to a lumbar vertebral body.

The implant 10 serves as replacement for the left side of the pelvis 1. Corresponding to the native structure of the pelvis, it comprises an ilium portion 12, an ischium portion 13, a pubic bone portion 14, and an acetabulum portion 15. It will be clear to the skilled person that the implant may replace less, more or different parts of the pelvis depending on the medical situation of a patient.

Figure 2:
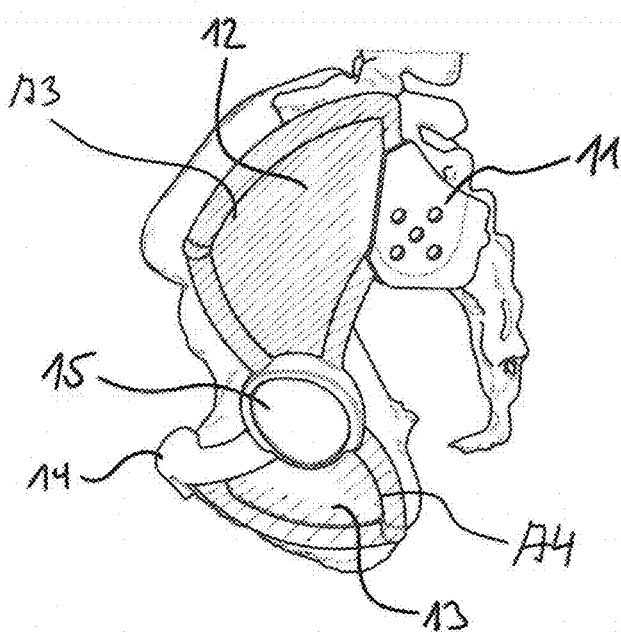
FIG. 2 illustrates a lateral view of the implant shown in FIG. 1.

FIG. 2 shows the implant 10 of FIG. 1 from a lateral perspective. This perspective visualizes the posterior side of the ilium portion 12 and of the ischium portion 13. The implant 10 also comprises a first bone attachment portion 11 that is configured for contact with the skeletal structure of the patient, in particular between the ilium portion 12 and the sacrum 6. Similarly, the second bone attachment portion 16 with a surface area B2 that is configured for a connection between the pubic bone portion 14 of the implant 10 and the pubic bone 4 of the native pelvis 1. The connection between the bone tissue and the surface areas B1 and B2 of the bone attachment portions 11 and 16, respectively, is achieved by ingrowth or apposition of bone tissue.

Figure 3:
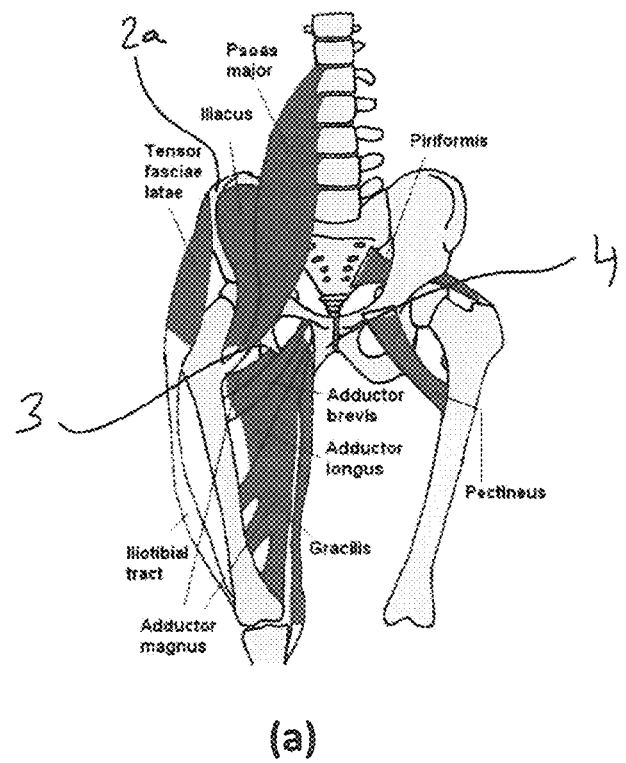
Figure 3:
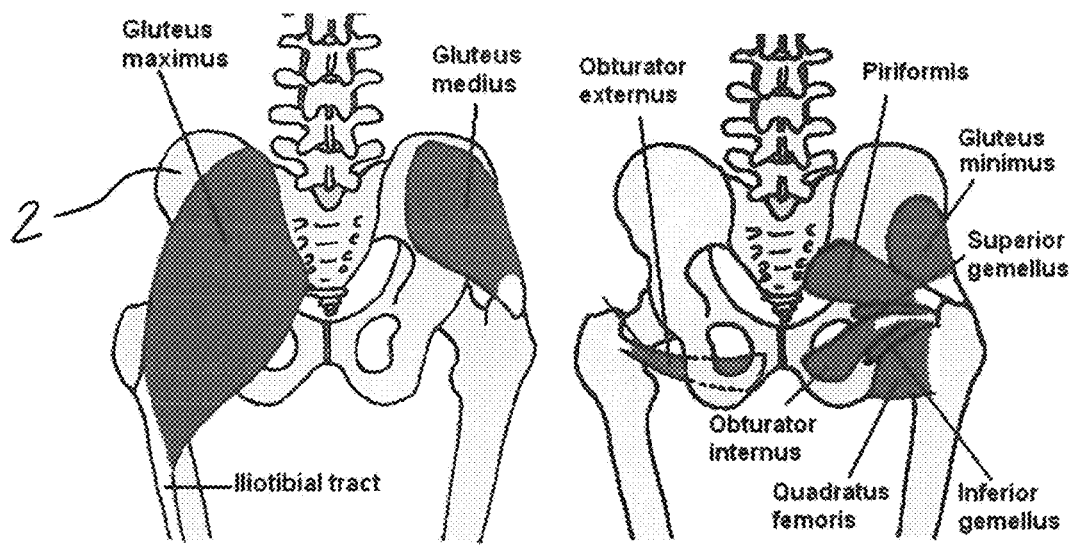

FIG. 3 is a schematic view of the anterior side of the pelvis. As this figure illustrates, there are muscles attached to the ilium 2, the ischium 3, and the pubic bone 4. As shown in FIGS. 3b and 3c, there are also numerous muscles attached to the posterior side of the ilium 2, in particular the gluteus maximus, and the ischium 3. These muscles are responsible for the different movements of the legs, i.e. flexion, extension, rotation, adduction, and abduction.

In the example of a partial replacement of the pelvis by an implant 10, these muscles as well as tendons and ligaments on the posterior and anterior side of the ilium 2 and the ischium 3 have to be separated at least from the bone tissue that is to be removed during surgery.

In order to restore as much of the skeletal movability and stability as possible, these soft connective tissue structures should be attached to the implant. As already described above, this may be achieved by removing the soft connective tissue structures including the periosteum they are attached to. Subsequently the periosteum can be placed on the implant's outer surface for attaching these structures to the implant 10. In this respect, it is desirable to achieve a firm attachment by growth of soft connective tissue or at least an attachment of connective tissue by a mechanical connection with the respective surface area's surface topography to the implant 10.

In order to achieve this objective, the implant 10 comprises at least one of the surface areas A1 to A4, which is coated and, thus, configured for contact with soft connective tissue. The surface areas A1 to A4 are indicated in FIGS. 1 and 2 by a diagonally hatched area. It is particularly preferred to apply the coating forming the first surface area to the posterior side of the pelvic implant 10, i.e. at least to the areas designated as A3 and A4 in FIG. 2, since the connective tissue to be attached in this region (cf. FIGS. 3b and 3c) is particularly important for the stability of the implant position.

As described above, it is advantageous to cover the implant's surface as much as possible in order to provide for a good attachment of the soft connective tissue structure. Nonetheless, an implant may have area, where a smooth or polished surface is advantageous. This is for example the case for the surface area C of the anterior side of the ilium portion 12. On this side, internal organs such as intestines are supported by the implant 10. Thus, any significant surface roughness may cause irritations or even injuries to these organs. However, a smooth or polished surface area C can prevent such an undesirable outcome.

In the embodiment of an implant 10 as shown in FIGS. 1 and 2, the coated surface area, i. e. the first surface area A1 to A4, is formed using a first material for the coating comprising tantalum, i. e. pure tantalum or a tantalum alloy. As described above, the first material is applied to the implant body of the implant 10 as a coating. Nonetheless, one may also consider using the first material as basic material to form at least parts of the implant 10 if the material comprising tantalum, i. e. pure tantalum or a tantalum alloy, has the strength to withstand the forces the implant 10 will be exposed to.

Nonetheless, forming the implant body of the implant 10 with a second material has the advantage that an established material for replacing a bone structure and/or for anchoring an implant may be used, such as titanium, CoCr, Mo, alloys containing these components, such as stainless steel.

Preferably, the second material is titanium or a titanium alloy since this material fosters the ingrowth of bone and provides a reliable and strong attachment of an implant 10 to the skeletal structure of a patient. More specifically, the material provides the boundary conditions for osteoblasts to create bone tissue that grows on or into the implant's surface topography.

Alternatively, the basic material for the implant body of the implant 10 and the material configured for contact with bone may differ. For example, titanium or a titanium alloy may be applied as a coating as well. This way only a bone attachment portion such as the first bone attachment portion in FIGS. 1 and 2 may be configured as a second surface area that fosters bone ingrowth. Such a configuration has the advantage that both bone ingrowth and the ingrowth of soft connective tissue structures can be enhanced in specific surface areas, where the attachment of these tissues to the implant 10 is desirable.

The second material forms the outer surface of the second surface area. If the second material is the basic material of the implant 10, i. e. it is the material that forms the basic shape of the implant 10, any portion of the implant body may form a second surface area.

After production of the implant 10, the first material is applied as a coating so that a first surface area A1 to A4 is formed on top of the outer surface of the implant body. The first material is preferably applied onto the implant body using chemical vapor deposition (CVD), physical vapor deposition (PVD) and/or vacuum plasma spraying (VPS). As described above, using these techniques, a coating on a predetermined portion of an implant surface with a uniform thickness can be applied without significantly affecting the properties of the material that forms the coating. In particular, the coating may be applied with a low thickness, such as the 2 to 10 µm and preferably 2 to 5 µm, so that a surface topography that is preferably created on the implant body beforehand is not altered significantly and still allows for a mechanical attachment of soft connective tissue. Such a surface topography may include a specific surface roughness and/or a porous surface structure.

Vacuum plasma spraying can be used to at least partly obtain the desired roughness and structure of the surface topography. Also, vacuum plasma spraying is able to provide a porous surface during the creation of the coating. Thus, using this technique, there may be no need for additional processing steps for establishing a surface topography on the implant's body.

The surface topography can also be created by removing material from the implant body or coating using an abrasive process such as abrasive blasting, in particular grit blasting. Nonetheless, it is also possible to achieve the desired surface topography using plasma spray application or any other surface modification. Nonetheless, preferably, the surface topography is created on the implant body and is, afterwards coated in the first surface area A1 to A4 with the tantalum coating. In this case, the surface topography for the surface areas A1 to A4 is preferably the same as for the surface areas B1 and B2. This facilitates production, in particular for an implant that only comprises surface areas configured for contact to soft connective tissue or bone tissue.

Additional features may be provided for the surgical attachment of soft connective tissue, such as holes or recesses. These additional features may be located in the first and/or remaining surface area of the implant 10.

The first surface area A1 to A4 is designed so that contact with soft connective tissue can result in its attachment to the implant. More specifically, the first surface area establishes an environment that is adapted for the proliferation and attachment of fibroblasts that have the capability for forming at least a mechanical connection between soft connective tissue structures and the implant's first surface area A1 to A4. As noted above, this can be additionally promoted by configuring the surface topography of the first surface area A1 to A4 for an attachment of soft connective tissue by providing a specific surface roughness and/or porosity. The inventors have found that an average surface roughness $R_a$ in the range between 5 to 9 µm, in particular 7 µm, is particularly apt for this type of tissue. Further, rendering the surface porous as described above allows additional mechanical anchoring of these structures in the implant's surface.

In comparison to the second surface area configured for contact with bone tissue, the first surface area A1 to A4 may have a lower surface roughness. This is for example the case if the first surface area has a surface roughness as described above, wherein the second surface area has a porous configuration.

Nonetheless, the above-noted surface roughness for the first surface area is advantageous for the ingrowth of soft connective tissue structures into the implant's surface and may still be combined with a porous surface. In addition to other attachment mechanisms, such as focal adhesion, the soft connective tissue structures also get anchored in the first surface area by virtue of a form fit between the tissue and the surface topography, particularly if a porous surface topography is applied.

In contrast, the lower surface roughness alone may be less prone to the ingrowth of bone tissue since osteoblasts are attracted by the second surface area so that it is less likely that they spread to the first surface area(s) A1 to A4 of the implant 10, which may be unfavorable for the desired attachment of soft tissue in this area. Consequently, by choice of material and surface topography, it is possible to foster the ingrowth of soft connective tissue structures, yet to achieve an adverse effect on the ingrowth of bone and vice versa.

REFERENCE SIGNS 1 pelvis
2 ilium
2a ilium crest
3 ischium
4 pubic bone
5 acetabulum
6 sacrum
10 implant
11 first bone attachment portion
12 ilium portion
13 ischium portion
14 pubic bone portion
15 acetabulum portion
16 second bone attachment portion A1-A4 first surface area for soft connective tissue
B1, B2 second surface area for bone tissue
C third surface area for internal organs

The invention claimed is:

1. A pelvic implant comprising an implant body with a first surface area configured for contact with soft connective tissue and a second surface area configured for contact with bone tissue, wherein
    the first surface area is covered by a coating comprising tantalum and
    a second surface that is not tantalum, wherein
    the first surface area covers at least 30% of the entire surface of the implant
    wherein the coating of the first surface area has a thickness of 2 to 10 µm.

2. Implant according to claim 1, wherein the coating covering the first surface area consists of pure tantalum.

3. Implant according to claim 1, wherein the second surface area is formed by the material forming the implant body.

4. Implant according to claim 1, wherein the first surface area comprises a surface topography that is generally formed by the surface of the implant body underneath the coating.

5. Implant according to claim 1, wherein the coating of the first surface area has a thickness of 2 to 5 µm.

6. Implant according to claim 1, wherein the structural material forming the second surface area comprises titanium, CoCr, Mo, alloys thereof, and stainless steel.

7. Implant according to claim 1, wherein the second surface area has the same surface topography as the first surface area.

8. Pelvic implant according to claim 1, wherein the first surface area covers at least 50% and preferably at least 70% of the entire surface of the implant.

9. A pelvic implant comprising an implant body with a first surface area configured for contact with soft connective tissue and a second surface area configured for contact with bone tissue, wherein the first surface area is covered by a coating comprising tantalum and the outer surface of the second surface area is formed by a material, which is different than the one of the coating covering the first surface area, wherein the first and/or the second surface area is porous, preferably with a pore size of 40 to 800 µm.

10. A pelvic implant comprising an implant body with a first surface area configured for contact with soft connective tissue and a second surface area configured for contact with bone tissue, wherein the first surface area is covered by a coating comprising tantalum and the outer surface of the second surface area is formed by a material, which is different than the one of the coating covering the first surface area, wherein the first surface area has an average surface roughness in the range of 2 to 3 82 m and at maximum 7 µm, preferably 5 µm.

* * * * *